United States Patent [19]

Houlihan et al.

[11] Patent Number: 4,992,428

[45] Date of Patent: Feb. 12, 1991

[54] 5-ARYL-SUBSTITUTED-2,3-DIHYDRO-IMIDAZO[1,2-a]FURO- AND THIENO PYRIDINES

[75] Inventors: William J. Houlihan, Mountain Lakes; Seung H. Cheon, Glen Ridge, both of N.J.

[73] Assignee: Sandoz Pharm. Corp., E. Hanover, N.J.

[21] Appl. No.: 363,794

[22] Filed: Jun. 9, 1989

Related U.S. Application Data

[63] Continuation-in-part of Ser. No. 331,939, Mar. 31, 1989, abandoned, which is a continuation-in-part of Ser. No. 263,667, Oct. 27, 1988, abandoned, which is a continuation of Ser. No. 190,566, May 5, 1988.

[51] Int. Cl.$^5$ .............. A61K 31/34; A61K 31/38; A61K 31/435; C07D 491/14
[52] U.S. Cl. .................. 514/63; 514/228.5; 514/233.2; 514/255; 514/293; 514/212; 544/60; 544/126; 544/361; 540/599; 546/14; 546/84

[58] Field of Search ............... 546/14, 84; 514/293, 514/228.5, 233.2, 255, 212; 544/126, 60, 361; 540/599

[56] References Cited

U.S. PATENT DOCUMENTS 4,100,165  7/1978  Houlihan ............... 546/84
4,101,553  7/1981  Houlihan ............... 546/84
4,279,912  7/1981  Ager et al. ............ 544/126

Primary Examiner—Mary C. Lee
Assistant Examiner—J. Richter
Attorney, Agent, or Firm—Gerald D. Sharkin; Robert S. Honor; Joseph J. Borovian

[57] ABSTRACT

The invention discloses certain 5-aryl-substituted,2,3-dihydro-imidazo[1,2-a]furo- and thieno pyridines useful as PAF receptor antagonists and for treating tumors, pharmaceutical compositions containing said compounds as an active ingredient thereof and a method of using such compositions for inhibiting PAF-mediated bronchoconstriction and extravasation, for controlling hyperreactive airways, for protecting against endotoxin-induced hypotension and death and for treating tumors.

20 Claims, No Drawings

5-ARYL-SUBSTITUTED-2,3-DIHYDRO-IMIDAZO[1,2-a]FURO- AND THIENO PYRIDINES

This is a continuation-in-part of U.S. patent application Ser. No. 07/331,939, filed Mar. 31, 1989, which in turn is a continuation-in-part of U.S. patent application Ser. No. 07/263,667, filed Oct. 27, 1988, which in turn is a continuation of U.S. patent application Ser. No. 07/190,566, filed May 5, 1988, all of which are now abandoned.

The present invention relates to 5-aryl-sustituted-2,3-dihydro-imidazo[1,2-a]furo- and thieno pyridines and to their use as platelet activating factor (PAF) receptor antagonists and anti-tumor agents. The invention also relates to pharmaceutical compositions containing the afore-mentioned compounds as an active ingredient thereof and to the method of using such compositions for inhibiting PAF-mediated bronchoconstriction and extravasation, for controlling hyperreactive airways induced by PAF or allergen, for protection against endotoxin-induced hypotension and death and in treating tumors.

U.S. Pat. No. 3,887,566 discloses certain 2,3-dihydroimidazoisoquinolines exhibiting analgesic, anti-inflammatory, anti-bacterial, anti-viral and cardiovascular properties. U.S. Pat. No. 4,100,165 discloses certain 5-hydroxy-2,3,5,6-tetrahydrofuran imidazo[2,1-a]isoquinolines containing a pyridyl-, thienyl- or furyl ring in the 5-position, which compounds are useful as anorexics and anti-depressants. U.S. Pat. No. 4,101,553 discloses certain 5-hydroxy-2,3,5,6-tetrahydrofuran imidazo[2,1-a]isoquinolines containing an optionally substituted aryl group in the 5-position, said compounds useful as anorexics and anti-depressants. WO 88/00587 discloses certain 5-hetero- or aryl-substituted-imidazo[2,1-a]isoquinolines which are useful as PAF receptor antagonists and as anti-tumor agents.

The essence of the present invention is the discovery that certain 5-aryl-substituted-2,3-dihydro-imidazo[1,2-a] furo- and thieno pyridines of formula I:

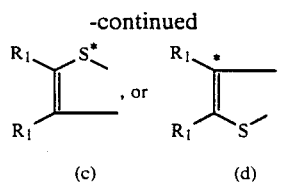

I wherein
each R is, independenly, hydrogen or methyl;
T is

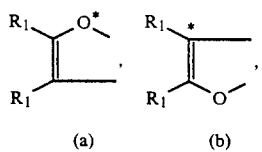

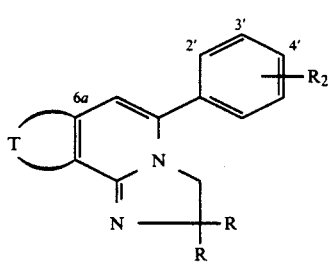

where
each $R_1$ is hydrogen or methyl, and * indicates the atom attached to the 6a-position of the tricyclic ring; and
$R_2$ is straight or branched chain $C_1$–6alkyl; tri-$C_1$–3alkylsilyl; a group of the formula

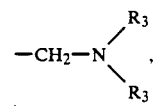

where each $R_3$, independently, is straight or branched chain $C_1$–4alkyl, or the two $R_3$'s together with the nitrogen atom to which they are attached form a group of the formula

where n is an integer 4, 5 or 6, or a group of the formula

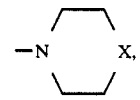

where X is —O—, —S— or —NCH$_3$; or a group of the formula

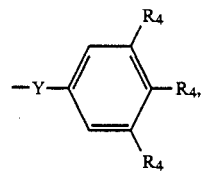

where Y is $+CH_2+_{1-3}$, —OCH$_2$— or —OCH$_2$CH$_2$—, and each $R_4$, independently, is hydrogen or $C_{1-3}$alkoxy; with the provisos that:

(1) only one of the $R_1$'s in (a), (b), (c) or (d) is methyl; and
(2) the $R_2$ substituent can only be in the 3'- or 4'-positions;

and their pharmaceutically acceptable acid addition salts, where such may exist, are useful as PAF receptor antangonists and in treating tumors.

Of the compounds of formula I, preferred are the compounds of formula I':

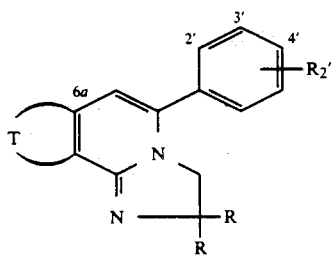

where $R_2^1$ is straight or branched chain $C_{1-4}$alkyl; tri-$C_{1-3}$alkylsilyl; a group of the formula

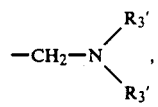

where the $R_3^1$'s are the same and are straight chain $C_{1-4}$alkyl, or the two $R_3^1$'s together with the nitrogen atom to which they are attached form a group of the formula

where n is as defined above, or a group of the formula

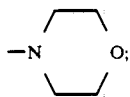

or a group of the formula

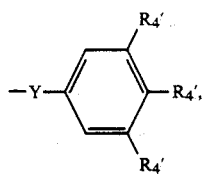

where Y is as defined above and the $R_4^1$'s are the same and are $C_{1-3}$alkoxy; and the R's and T are as defined above, and the foregoing provisos apply; and their pharmaceutically acceptable acid addition salts, where such may exist.

The more preferred compounds of formula I are those of formula I":

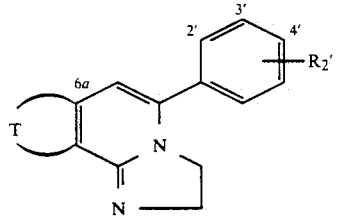

wherein T and $R_2^1$ are as defined above, and the foregoing provisos apply; and their pharmaceutically acceptable acid addition salts, where such may exist.

The above-identified compounds of formula I may be prepared according to the following reaction scheme:

REACTION A

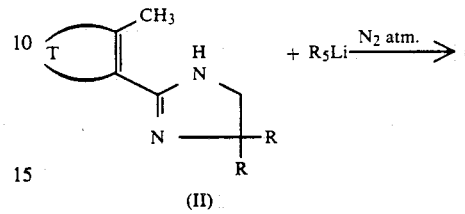

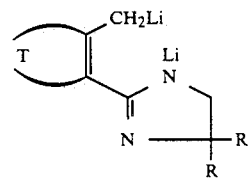

where $R_5$ is straight or branched chain $C_{1-4}$alkyl, T is (a), (b), (c) or (d) as defined above and the R's are as defined above.

REACTION B

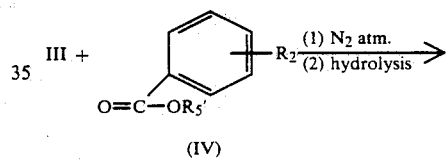

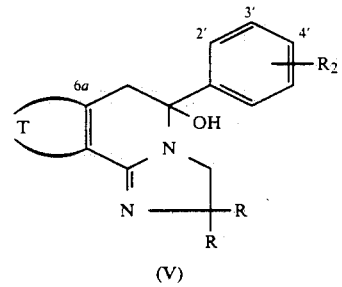

where $R_5^1$ is straight chain $C_{1-4}$alkyl, and T, $R_2$ and the R's are as defined above.

REACTION C

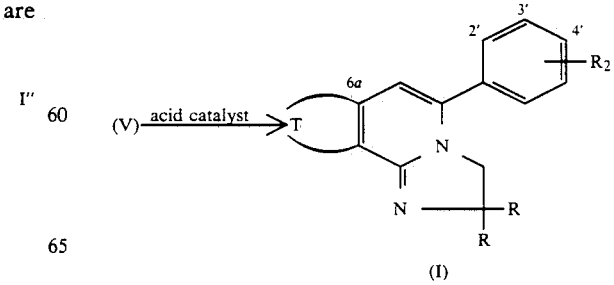

where t, $R_2$ and the R's are as defined above.

With respect to the individual reactions, Reaction A concerns the reaction of a compound of formula II with a $C_{1-4}$alkyl lithium compound (preferably straight chained) under a nitrogen atmosphere to yield a compound of formula III. The reaction is generally carried out in the presence of an inert, organic solvent, e.g., an aliphatic hydrocarbon such as heptane, hexane and the like, an aliphatic ether such as diethyl ether, or a cyclic ether such as tetrahydrofuran. Optionally, a complexing or activating agent for the lithium compound, e.g., tetramethylethylenediamine, is added to the reaction. As to the temperature and time of the reaction, a temperature in the range of between 0° and −78° C., preferably between −50° and −78° C., for a period of between 10 minutes and 2 hours is most suitable.

Reaction B involves, in a first step, the reaction of a compound produced in Reaction A, i.e., a dilithiated compound of formula III, with a compound of formula IV under a nitrogen atmosphere. As with Reaction A, the first step of Reaction B is conducted in the presence of an aliphatic hydrocarbon such as hexane, heptane and the like, an aliphatic ether such as diethyl ether, or a cyclic ether such as tetrahydrofuran. The first step of Reaction B is conducted at a temperature in the range of −78° to 25° C., preferably −78° to 20° C., for a period of between 30 minutes and 6 hours. The adduct formed is then hydrolyzed in a second step to yield a compound of formula V. The hydrolysis is conducted in conventional manner, e.g., employing water, dlilute mineral acid, ammonium chloride solution and the like. The temperature and time of the reaction with respect to hydrolysis is not critical.

In Reaction C, a compound produced in Reaction B, i.e., a compound of formula V, is dehydrated in an inert, organic solvent in the presence of an acid catalyst to yield the desired compound of formula I. The acid catalyst employed can be any mineral acid such as hydrochloric acid, sulfuric acid, phosphoric acid and the like, or an organic acid, e.g., an alkylcarboxylic acid such as acetic acid, an arylcarboxylic acid such as benzoic acid, an alkylsulfonic acid such as methanesulfonic acid or an arylsulfonic acid such as p-toluenesulfonic acid. The preferred acid catalysts are alkylcarboxylic acids, more preferably, acetic acid, and arylsulfonic acids, more preferably, p-toluenesulfonic acid. The inert solvent is usually an aliphatic hydrocarbon such as hexane, heptane and the like, an aromatic hydrocarbon such as benzene, toluene and the like, a chlorinated hydrocarbon such as chloroform, methylene chloride and the like, an aliphatic ether such as diethyl ether, a cyclic ether such as tetrahydrofuran, or an excess of a liquid acid catalyst, preferably acetic acid, or p-toluenesulfonic acid may serve as the solvent. The temperature at which the dehydration is conducted is not critical, however, a temperature in the range of between 35° and 200° C.; preferably between 75° and 120° C., is most suitable. As with the temperature, the time of the reaction is not critical, however, it is preferred that the dehydration be conducted for a period of between 3 and 24 hours, preferably between 4 and 20 hours.

The compounds of formulae II and IV are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile) or fractional distillation under high vacuum (if sufficiently volatile). Often however, the crude product of one reaction may be employed in the following reaction without purification.

As is evident to those skilled in the art, certain of the compounds of formula I can exist as stereoisomers and such isomers and their enantiomers are contemplated as being included within the scope of this invention. Moreover, certain of the compounds of formula I can exist as optical isomers and such isomers are also contemplated as being included within the scope of this invention.

As previously indicated, pharmaceutically acceptable acid addition salts (i.e., those salts which do not significantly increase the toxicity of the base compounds) of the compounds of formula I, where such may exist, are included within the cope of this invention. These include salts of mineral acids such as hydrochloric, hydrobromic, phosphoric and sulfuric acids, as well as salts of organic acids such as tartaric, acetic, citric, malic, maleic, methanesulfonic and gluconic acids.

All of the compounds of formula I, as well as their pharmaceutically acceptable acid addition salts, are useful as platelet activating factor receptor antagonists as indicated by their ability to inhibit specific binding of [$^3$H]-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 ug/ml of Prostaglandin $I_2$ ($PGI_2$) in a ratio of blood to anti-coagulant of 9:1. Platelet rich plasma (PRP) is prepared by centrifugation ($250 \times g$) of the blood for 20 minutes at room temperature. The PRP is then centrifuged ($900 \times g$) for 10 minutes at room temperature and the platelet pellet is washed two times with Tris-Tyrode's (TT) solution having a pH of 7.4 and containing 0.25% bovine serum albumin (BSA), and to which has been added $PGI_2$ at a final concentration of 0.3 ug/ml. The platelets are resuspended at 350,000/ul in TT/BSA containing 1.4 mM $CaCl_2 \cdot 2H_2O$ and 0.7 mM $MgCl_2 \cdot 6H_2O$. All of the tests are conducted in duplicate and each of the test compounds is evaluated at concentrations of 100, 50, 1 and 0.1 uM. For each determination, the following solutions are mixed:

500 ul of the above-described platelets;
10 ul of ($^3$H)-PAF (40,000 counts per minute (cpm) to a final concentration of 1.5 uM); and either
10 ul of the test compound at 50 x the desired final concentration,
10 ul of vehicle (total bound), or
10 ul of $1.85 \times 10^{-5}$M cold PAF (non-specifically bound).

Each mixture is allowed to incubate at room temperature for one hour, after which time the reaction is terminated by the addition of 500 ul of ice cold TT/BSA and centrifugation ($900 \times g$) at 4° C. for 10 minutes. The resultant supernatant is aspirated into scintillation vials and the pellet is washed with 250 ml. of ice cold TT/BSA centrifuged ($900 \times g$) at 4° C. for 10 minutes. The supernatants are then aspirated into the same scintillation vials as before and 10 ml. of Scintiverse II (a liquid scintillation cocktail) is added to and mixed therewith. The pellets are resuspended in 500 ul of Scintiverse II and mixed well. An additional 2 ml of Scintiverse II is then added to the vials and, after mixing, the vials are counted for 1 minute in a liquid scintillation spectrometer. The amount of specific binding is calculated as the difference in cpm between the total bound

[³H]-PAF and non-specifically bound [³H]-PAF. The percent inhibition of specific binding is determined by dividing the cpm specifically bound in the presence of the test compound by the cpm specifically bound in total, multiplying by 100 and then subtracting from 100. An $IC_{50}$ (50% inhibitory concentration) value is generated by evaluating the test compound over the full concentration range.

Moreover, in view of their usefulness as PAF receptor antagonists, the compounds of formula I, and their pharmaceutically aceptable acid addition salts, have been found useful as inhibitors of PAF-mediated bronchoconstriction, which property was evaluated by the PAF-induced Pulmonary Inflation Pressure (PIP) Increase test (Test B) as follows:

Male guinea pigs, weighing between 300 and 400 gm, are anesthetized, after which time trachea tube, carotid and jugular cathethers are inserted. The test animal is then force ventilated employing a small animal Harvard respirator and the resistance to lung inflation (PIP) is measured utilizing a pressure transducer and recorder. The test compound is administered orally at 30 minutes prior to, intravenously (jugular) at 5 minutes prior to, or intraarterially at 1 to 5 minutes prior to the introduction of PAF. The PAF ($C_{18}$-Sandoz, Hanover) is dissolved in Tris-Tyrode's bovine serum albumin buffer and administered intravenously (jugular) at 100 ng/kg. Any blood pressure measurements taken are recorded from a transducer attached to the carotid catheter. Two responses are noted in the PIP recordings after the PAF is administered: 1) an immediate response which, in PAF-only treated test animals, averages out to between 70% and 80% more than the baseline PIP values. (This early response is also the greatest response and is, therefore, termed maximal PIP); and 2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been administered PAF and the test compound compared to the test animal to which only PAF has been administered to generate an ED 50 (dose needed to effect a 50% response).

Furthermore, the compounds of formula I and their pharmaceutically acceptable acid addition salts, are useful as inhibitors of PAF-mediated extravasation (the extrusion of plasma from the lumen of the blood vessels into the vessel wall and surrounding tissues) measured as a function of hemoconcentration according to the PAF-induced Extravasation test (Test C) as follows:

Male guinea pigs, weighing between 300 and 400 gm, are anesthetized, after which time a femoral catheter is inserted. The test compound is administered intraarterially at one to five minutes prior to the introduction of PAF. The PAF ($C_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 ul heparinized hematocrit tubes. These samples are taken just prior to the injection of PAF, one minute subsequent to the injection of PAF and every two minutes thereafter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hematocrit values obtained with the test compound are compared to the hemocentration values obtained with PAF alone and are expressed as percent inhibition of percent increase in hematocrit. From the values obtained, an $ED_{50}$ is generated.

Still further, the compounds of formula I, and their pharmacutically acceptable acid addition salts, are useful in controlling hyperreactive airways induced by PAF or allergen, which property can be measured in accordance with the following procedure (Test D):

Male Hartley guinea pigs weighing 250 gm are sensitized to ovalbumin by aerosol inhalation exposure. The test animals are then subsequently rechallenged with ovalbumin aerosol repeatedly (3 to 6 times) over a period of two to three weeks. Airway reactivity is assessed by an acetylcholine dose response curve at times (1 to 3 days) after the last ovalbumin exposure. The test compound is assessed for its ability to control hyperreactivity airways by administering it orally with a gavage tube in an acceptable vehicle prior to each ovalbumin antigen exposure.

Yet still further, the compounds of formula I, and their pharmaceutically acceptable acid addition salts, are useful in protecting against endotoxin-induced hypotension, which property can be measured according to the following procedure (Test E):

Male Sprague-Dawley rats weighing between 250 and 270 gm are anesthetized with sodium pentobarbital (50 mg/kg i.p.) and the left common carotid artery is cannulated (PE-50 tubing) and connected to a P50 pressure transducer. Mean arterial pressures and diastolic and systolic measurements are recorded using a Gould 2400S physiograph. Blood flow of the mesenteric artery is measured on a calibrated electromagnetic flowmeter probe. Blood is collected via the femoral artery into heparinized capillary tubes and centrifuged to determine hematocrit values.

Endotoxin from E. coli serotype 0111:$B_4$ is prepared fresh daily and administered by i.v. injection to the test animals in tris-Tyrode's buffer over a 1 to 50 mg/kg dosage range to establish a dose-response profile. The administration of endotoxin at 15 mg/kg i.v. produced a 54±8% decrease in mean arterial pressure and a corresponding 80% decrease in mesenteric artery blood flow. The test compound is assessed for its ability to protect against endotoxin-induced hypotension by administering it intravenously after endotoxin administration and measuring the recovery of blood pressure and mesenteric artery blood flow. The $ED_{50}$ value of the test compound is determined using linear regression fitting of inhibition profiles from 5 to 6 doses (3 animals per dose).

Yet even still further, the compounds of formula I, and their pharmaceutically acceptable acid addition salts, are useful in protecting against endotoxin-induced death, which property can be measured according to the following procedure (Test F):

Healthy male BALB/c mice weighing between 24 and 27 g. are allowed to acclimate for 1 week with access to food and water. The test animals are then placed in a ventilated plexiglass restrainer that allows access to the tails. After the tails are allowed to immerse in warm water (38° C.) for 30 seconds, endotoxin from E. coli serotype 0111:B4 is administered in a single injection at 2 ml/kg body weight to produce lethality at the desired effect of LD 70-90. The test compound is assessed for its ability to protect against endotoxin-induced death by administering it orally in a single bolus at a volume of 1 ml/kg body weight. Each treatment group consists of 7 to 10 test animals, every dosage is considered as a separate group and control groups are dosed with vehicles (water, tris-Tyrode's buffer, 1% CMC, etc) only. The percent mortality (or survival) is expressed by the number of deaths (or survivors) within the observation period. Values obtained are mean and standard error of mean of a single treatment which represents multiple days results for reproducibility. The $ED_{50}$ value of the test compound is determined using a Students t test (2 tail) for significance.

The precise dosage of a compound of formula I, or a pharmaceutically acceptable acid addition salt thereof, to be employed in treating PAF-mediated bronchoconstriction and extravasation, for controlling hyperreactive airways induced by PAF or allergen and protecting against endotoxin-induced hypotension and death depends upon several factors including the host, the nature and severity of the condition being treated, the mode of administration and the particular compound employed. However, in general, satisfactory inhibition or antagonism of PAF-mediated bronchoconstriction and extravasation, control of hyperreactive airways induced by PAF or allergen and protection against endotoxin-induced hypotension and death is achieved when a compound of formula I, or a pharmaceutically acceptable acid addition salt thereof, is administered orally at a daily dosage of 0.2-100, preferably 0.2-50 mg/kg body weight or, for most larger primates, a daily dosage of 100-2000 mg, preferably 10-350 mg. A typical oral dosage is 50 or 100 mg, two or three times a day.

As indicated above, all of the compounds of formula I, and their pharmaceutically acceptable acid addition salts, are anti-tumor agents and, therefore, are useful in inhibiting the growth of various lymphomas, sarcomas, myelomas and leukemia cell lines. The ability of the compounds in treating tumors can be measured by the Tumor Cell Cytotoxicity test (TCC test) as follows:

In flat bottom microtiter plates (Nunc Roskieide, Denmark) are placed Abelson 8.1 tumor cells in DMEM +10% fetal calf serum and the tumor cell-containing plates are incubated with 1, 3 and 5 ug of the test compound for a period of 6 to 72 hours. The number of viable tumors cells can be determined by measuring the alkaline phosphatase in the following manner. The tumor cell plates are centrifuged (500×g.) for ten minutes and the supernatant flicked off. Without further washing, 100 ul of buffer containing 20 ul of diethanolamine, 2 uM of $MgCl_2.6H_2O$, 2.5 uM of p-nitrophenylphosphate and 10 mg Triton X-100 are added. The samples are incubated for 60 minutes at room temperature and the enzymatic reaction is terminated by the addition of 100 ul of 0.5N NaOH. The absorbance can then be measured at 405 nM using a Titertek Multiskan apparatus.

The anti-tumor activity of the compounds of formula I, and their pharmaceutically acceptable acid addition salts, may also be demonstrated employing the Influence on Cytotoxicity of $ET-18-OCH_3$ test (IC-ET test) as follows:

Bone marrow cell macrophages ($10^5$/well) obtained from [BALB/CX57/BL6]F1 mice are incubated with 10 ug of (±)-1-octadecyl-2-methoxy-3-phosphoryl choline ($ET-18-OCH_3$) for 24 hours in flat bottom microtiter plates (Nunc Roskieide, Denmark), after which time they are centrifuged and washed once. Abelson 8.1 tumor cells in DMEM+10% fetal calf serum and 1, 3 and 5 ug of the test compound are then added to the plates. With the cytotoxicity of $ET-18-OCH_3$ (10 ug) alone set at 100%, the inhibition or enhancement of the cytotoxic effect, as measured by an alkaline phosphatase assay, can be determined and values recorded after 72 hours for 1,3 and 5 ug of the test substance.

The usefulness of the compounds of formula I, and their pharmaceutically acceptable acid addition salts, in treating tumors may additionally be demonstrated employing the following procedure:

Meth A fibrosarcoma cells are induced in BALB/C mice by administering methylcholanthrene according to the procedure of Old, et al. (L. J. Old, E. A. Boyse, D. A. Clarke, and E. Carswell, Ann. N.Y. Acad. Sci., 101,: 80 (1962). These tumor cells are harvested from the peritoneal cavity 10 to 12 days after administration of methylcholanthrene. Ten $CBF_1$ mice of 10-12 week age are each implanted with $7.3 \times 10^6$ Meth A sarcoma cells to serve as control. A second group of ten $CBF_1$ mice are each implanted with $7.3 \times 10^6$ Meth A sarcoma cells and on day one after implant each mouse is treated p.o. with 5-50 ug of the test compound per day for a total of twenty or twenty-seven days. Tumor growth and survivors are assayed on days 7, 14, 21 and 28 after tumor implantation.

As with the PAF inhibition use, the precise dosage of a compound of formula I, or a pharmaceutically acceptable acid addition salt thereof, to be employed for inhibiting tumors depends upn several factors including the host, the nature and the severity of the condition being treated, the mode of administration and the particular compound employed. However, in general, satisfactory inhibition of tumors is achieved when a compound of formula I, or a pharmaceutically acceptable acid addition salt thereof, is administered orally or intravenously at a daily dosage of 10-100, preferably 5-35 mg/kg body weight or, for most larger primates, a daily dosage of 500-2000 mg, preferably 1000-1500 mg. A typical oral dosage is 400 mg, two to three times a day, or 20 mg/kg intravenously over a 24 hour period.

Regardless of use, a small dosage is gradually increased until the optimal dosage for the host under treatment is determined. For administration by injection, a dosage somewhat lower than would be used for oral administration of the same compound to the same host having the same condition is usually employed.

A typical dosage unit for oral administration in PAF inhibition may contain 2.5 to 500 mg of a compound of formula I, or a pharmaceutically acceptable acid addition salt thereof, whereas for inhibition of tumors, a typical dosage unit for oral administration may contain 300 to 600 mg of a compound of formula I, or a pharmaceutically acceptable acid addition salt thereof. Preferred oral dosage units for PAF inhibition contain 5 to 200 mg, especially 10 to 100 mg of a compound of formula I, or a pharmaceutically acceptable acid addition salt thereof, whereas preferred oral dosage units for inhibition of tumors contain 300 to 500 mg, especially 350 to 450 mg of a compound of formula I, or a pharmaceutically acceptable acid addition salt thereof.

The compounds of formula I, and their pharmaceutically acceptable acid addition salts, may be combined with one or more pharmaceutically acceptable carriers and, optionally, one or more other conventional pharmaceutical adjuvants and administered orally in the form of tablets, dispersible powders, granules, capsules, elixirs, suspensions and the like or parenterally in the form of sterile injectable solutions or suspensions. The compositions may be prepared by conventional means.

The compounds of formula I, and their pharmaceutically acceptable acid addition salts, may be formulated into such pharmaceutical compositions containing an amount of the active substance that is effective in treating platelet activating factor-mediated bronchoconstriction and extravasation, for controlling hyperreactive airways induced by PAF or allergen, in protecting against endotoxin-induced hypotension and death and in treating tumors, such compositions in unit dosage form and such compositions comprising a solid pharmaceutically acceptable carrier.

Tablets and capsules containing the ingredients indicated below may be prepared by conventional techniques and are useful in treating platelet activating factor mediated bronchoconstriction and extravasation, for controlling hyperreactive airways induced by PAF or allergen and in protecting against endotoxin-induced hypotension and death. The tablet and capsule may be suitably administered two or three times a day.

| Ingredients | Weight (mg) tablet | capsule |
|---|---|---|
| compound of formula I, e.g., the compound of Example 4 | 50 | 50 |
| tragacanth | 10 | — |
| lactose (spray-dried) | 212.5 | 100 |
| corn starch | 15 | — |
| talcum | 10 | — |
| magnesium stearate | 2.5 | — |
| Total | 300.0 | 100 |

The following are representative of tablets and capsules which may be prepared by conventional means and are useful in treating tumors. The tablet may be administered two to four times a day whereas the capsule is suitably administered three times a day.

| Ingredients | Weight (mg) tablet | capsule |
|---|---|---|
| compound of formula I, e.g., the compound of Example 2 | 400 | 400 |
| tragacanth | 10 | — |
| lactose (spray-dried) | 197.5 | 250 |
| corn starch | 25 | — |
| talcum | 15 | — |
| magnesium stearate | 2.5 | — |
| Total | 650.0 | 650 |

The following pharmaceutical compositions are formulated with the indicated amount of active ingredient using conventional techniques. The injectable suspension and the oral suspension represent formulations useful as unit doses and may be administered in treating platelet activating factor mediated bronchoconstriction and extravasation, for controlling hyperreactive airways induced by PAF or allergin and in protecting against endotoxin-induced hypotension and death. The injectable suspension may be administered once or twice a day whereas the oral liquid suspension is suitiably administered three times a day.

| Ingredients | Weight (mg) sterile injectable suspension | oral liquid suspension |
|---|---|---|
| compound of formula I, e.g., the compound of Example 4 | 5 | 3 |
| sodium carboxymethylcellulose U.S.P. | 1 | 8 |
| methyl cellulose | 0.3 | — |
| polyvinylpyrrolidone | 2.7 | — |
| lecithin | 1.5 | — |
| benzyl alcohol | 0.01 | — |
| magnesium aluminum silicate | — | 25 |
| flavor | — | q.s. |
| color | — | q.s. |
| methyl paraben, U.S.P. | — | 3 |
| propyl paraben, U.S.P. | — | 0.7 |
| polysorbate 80 (e.g., Tween 80), U.S.P. | — | 5 |
| sorbitol solution, 70%, U.S.P. | — | 1450 |
| buffer agent to adjust pH for desired stability | q.s. for injection | q.s. |
| water | q.s. to 1 ml | q.s. to 5 ml |

The preferred pharmaceutical compositions from the standpoint of preparation and ease of administration are solid compositions, particularly liquid or hard-filled capsules and tablets containing from about 10 to 100 mg of the active ingredient concerning the PAF inhibition use and from about 350 to 450 mg: of the active ingredient with respect to tumor inhibition.

The following examples show representative compounds encompassed by this invention and their synthesis. However, it should be clearly understood that they are for purposes of illustration only.

EXAMPLE 1

2,3-Dihydro-8-methyl-5-[4'-[2-(3",4",5"-trimethoxyphenyl)ethyl]phenyl]imidazo[1,2-a]furo[3,2-c]pyridine

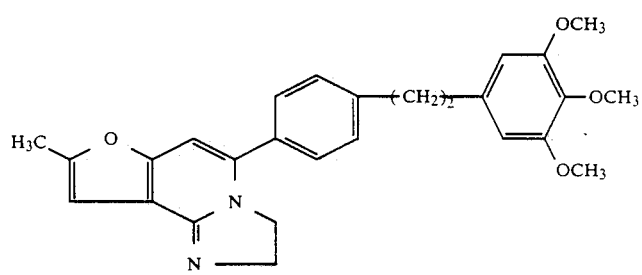

(a) Preparation of 2,3,5,6-tetrahydro-8-methyl-5-[4'-[2-(3",4",5"-trimethoxyphenyl)ethyl]phenyl]imidazo[1,2-a]furo[3,2-c]pyridin-5-ol To a solution of 1 g (6.1 mmol) of 2-(2',5'-dimethylfuran-3-yl)-4,5-dihydro-1H-imidazole in a mixture of 40 ml of dry tetrahydrofuran and 1.69 g (15 mmol) of N,N,N',N'-tetramethylethylenediamine was added, at −78° C. under a nitrogen atmosphere, 8.4 ml of a 1.6M solution of N-butyl-lithium in hexane, and the resultant mixture was stirred at −78° C. for 15 minutes. To this mixture was added a solution of 2 g (6.1 mmol) of methyl 4-[2-(3',4',5'-trimethoxyphenyl)ethyl]benzoate in 10 ml of dry tetrahydrofuran and the reaction mixture was allowed to warm to ambient temperature and then stirred at ambient temperature for 2 hours. The mixture was then quenched with saturated ammonium chloride solution and extracted with methylene chloride. The combined organic extracts were then washed successively with water and brine, dried over magnesium sulfate and filtered. The filtrate was then evaporated under reduced pressure to yield a yellow foam.

PREPARATION OF THE TITLE COMPOUND

To a solution of 2.8 g (6.1 mmol) of the compound prepared in (a) above in 100 ml of dry benzene was added 0.3 g of p-toluenesulfonic acid monohydrate and the resultant mixture was heated at reflux for 16 hours using a Dean-Stark trap to remove water. The reaction mixture was then cooled to room temperature, diluted with methylene chloride, washed successively with water, a saturated sodium bicarbonate solution and brine, dried over magnesium sulfate and filtered. The filtrate was then evaporated under reduced pressure and the crude product was purified by column chromatography on silica gel employing a mixture of methylene chloride and methanol in a 9:1 ratio as the eluent to yield the title compound as a tan solid foam.

EXAMPLE 2

2,3-Dihydro-8-methyl-5-[4'-[2-(3",4",5"-trimethoxyphenyl)ethyl]phenyl]imidazo[1,2-a]furo[3,2-c]pyridine, hydrochloride, hemihydrate

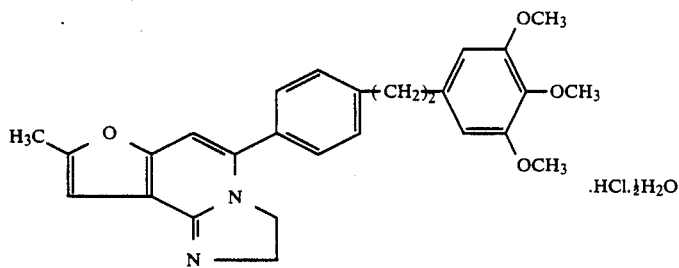

.HCl.½H₂O

Dry hydrochloride gas was bubbled into a solution of 0.4 g (0.9 mmol) of the compound of Example 1 in a mixture of 20 ml of dry ethanol and 5 ml of methylene chloride for 5 minutes. The excess gas and the solvents were evaporated under reduced pressure and the crude residue was purified by crystallization from a mixture of methylene chloride and ether to yield the title compound as a light tan solid, m.p. 220°-222° C.

Test A—IC$_{50}$—0.07 uM
Test B—38% inh. at 10 mg/kg p.o.
Test C—59% inh. at 10 mg/kg p.o.
TCC test—99.0% inh. at 5 ug after 72 hours
IC-ET test—99.9% enh. at 5 ug after 72 hours

EXAMPLE 3

2,3-Dihydro-5-[4'-[2-(3",4",5"-trimethoxyphenyl)ethyl]phenyl]imidazo[1,2-a]thieno[2,3-c]pyridine

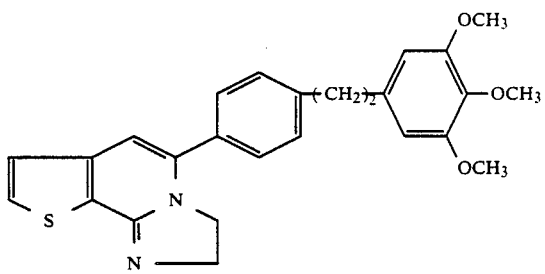

(a) Preparation of 2,3,5,6-tetrahydro-5-[4'-[2-(3",4",5"-trimethoxyphenyl)ethyl]phenyl]imidazo[1,2-a]thieno[2,3-c]pyridin-5-ol Following essentially the procedure of Example 1(a), and using in place of 2-(2',5'-dimethylfuran-3-yl)-4,5-dihydro-1H-imidazole, an approximately equivalent amount of 4,5-dihydro-2-(3'-methylthien-2-yl)-1H-imidasole, an orange foam was obtained.

PREPARATION OF THE TITLE COMPOUND

Following essentially the last step of the procedure for preparing the compound of Example 1, and using in place of the compound prepared in Example 1(a), an approximately equivalent amount of the compound prepared in (a) above, the title compound was obtained as a yellow foam.

EXAMPLE 4

2,3-Dihydro-5-[4'-[2-(3",4",5"-trimethoxyphenyl)ethyl]phenyl]imidazo[2,3-c]thieno[2,3-c]pyridine, hydrochloride, hemihydrate

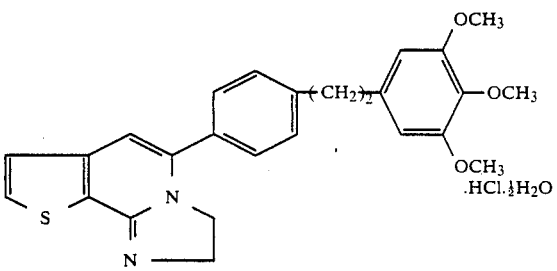

.HCl.½H₂O

Following essentially the procedure of Example 2, and using in place of the compound of Example 1, an approximately equivalent amount of the compound of Example 3, the title compound was obtained as a tan solid, m.p. 240°-242° C.

Test A—IC$_{50}$—0.01 uM
Test B—ED$_{50}$—1.0 mg/kg p.o.
Test C—ED$_{50}$—1.0 mg/kg p.o.
TCC test—98.4% inh. at 5 ug after 72 hours
IC-ET test—99.5% enh. at 5 ug after 72 hours

EXAMPLE 5

2,3-Dihydro-8-methyl-5-[4'-[2-(3'',4'',5''-trimethoxyphenyl)ethyl]phenyl]imidazo[1,2-a]thieno[3,2-c]pyridine

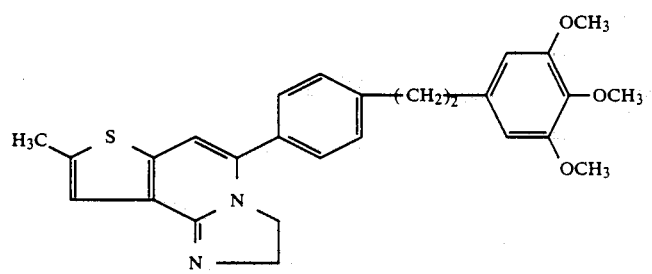

(a) Preparation of 2,3,5,6-tetrahydro-8-methyl-5-[4'-[2-(3'',4'',5'-trimethoxyphenyl)ethyl]phenyl]imidazo[1,2-a]thieno[3,2-c]pyridin-5-ol Following essentially the procedure of Example 1(a), and using in place of 2-(2',5'-dimethylfuran-3-yl)-4,5-dihydro-1H-imidazole, an approximately equivalent amount of 4,5-dihydro-2-(2',5'-dimethyl-3-thienyl)-1H-imidazole, a red foam was obtained.

PREPARATION OF THE TITLE COMPOUND

Following essentially the last step of the procedure for preparing the compound of Example 1, and using in place of the compound prepared in Example 1(a), an approximately equivalent amount of the compound prepared in (a) above, the title compound was obtained as an orange foam.

EXAMPLE 6

2,3-Dihydro-8-methyl-5-[4'-[2-(3'',4'',5''-trimethoxyphenyl)ethyl]phenyl]imidazo[1,2-a]thieno[3,2-c]pyridine, hydrochloride

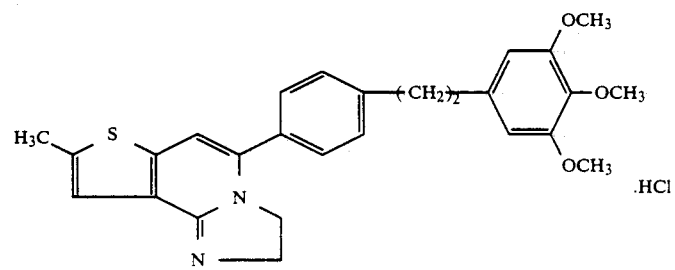

Following essentially the procedure of Example 2, and using in place of the compound of Example 1, an approximately equivalent amount of the compound of Example 5, the title compound was obtained as a tan solid, m.p. 245°-247° C.

EXAMPLE 7

2,3-Dihydro-8-methyl-5-[4'-t-butylphenyl]imidazo[1,2-a]thieno[3,2-c]pyridine

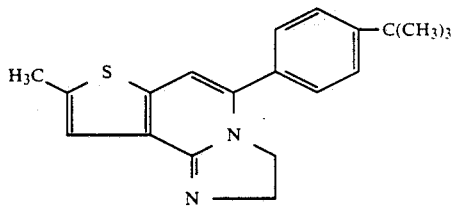

(a) Preparation of 2,3,5,6-tetrahydro-8-methyl-5-[4'-t-butylphenyl]imidazo[1,2-a]thieno[3,2-c]pyridin-5-ol Following essentially the procedure of Example 1(a), and using in place of methyl-4[2-(3',4',5'-trimethoxyphenyl)-ethyl]benzoate, an approximately equivalent amount of ethyl-p-t-butylbenzoate, an off-white solid was obtained.

Preparation of the Title Compound

Following essentially the last step of the procedure for preparing the compound of Example 1, and using in place of the compound prepared in Example 1(a), an approximately equivalent amount of the compound prepared in (a) above, the title compound was obtained as a light yellow solid.

EXAMPLE 8

2,3-Dihydro-8-methyl-5-[4'-t-butylphenyl]imidazo[1,2-a]-thieno[3,2-c]pyridine, hydrochloride

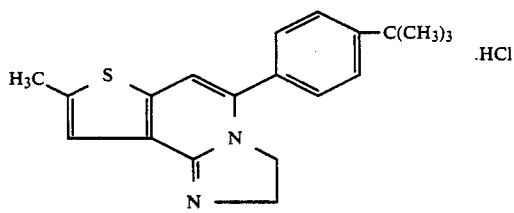

Following essentially the procedure of Example 2, and using in place of the compound of Example 1, an approximately equivalent amount of the compound of Example 7, the title compound was obtained as a light yellow solid, m.p.>280° C.

TCC test —99.8% inh. at 5 ug after 72 hours
IC-ET test —99.86% enh. at 5 ug after 72 hours

EXAMPLE 9

2,3-Dihydro-8-methyl-5-[4'-trimethylsilyphenyl]-imidazo[1,2-a]thieno[3,2-c]pyridine

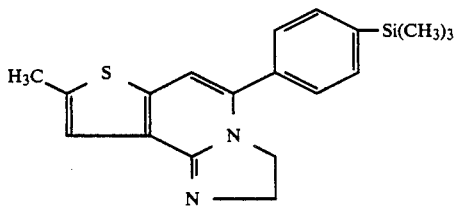

(a) Preparation of 2,3,5,6-tetrahydro-8-methyl-5-[4'-trimethylsilylphenyl-]imidazo[1,2-a]thieno[3,2-c]pyridin-5-ol Following essentially the procedure of Example 1(a), and using in place of methyl-4-[2-(3',4', 5'-trimethoxyphenyl)ethyl]benzoate, an approximately equivalent amount of methyl-p-trimethylsilylbenzoate, an off-white solid was obtained.

Preparation of the Title Compound

Following essentially the last step of the procedure for preparing the compound of Example 1, and using in place of the compound prepared in Example 1(a), an approximately equivalent amount of the compound prepared in (a) above, the title compound was obtained as an light yellow foam.

EXAMPLE 10

2,3-Dihydro-8-methyl-5-[4'-trimethylsilylphenyl-]imidazo[1,2-a]thieno[3,2-c]pyridine, hydrochloride

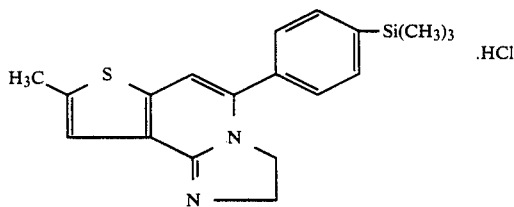

Following essentially the procedure of Example 2, and using in place of the compound of Example 1, an approximately equivalent amount of the compound of Example 9, the title compound was obtained as a light yellow solid, m.p.>280° C.

TCC test—99.8% inh. at 5 ug after 72 hours
IC-ET test—99.8% enh. at 5 ug after 72 hours

What is claimed is:

1. A compound of formula I:

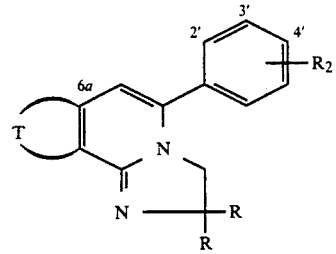

wherein
each R is, independently, hydrogen or methyl;
T is

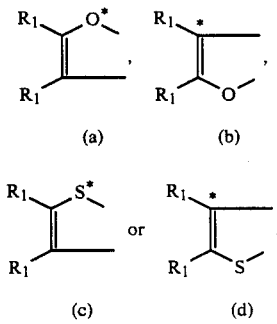

where
each $R_1$ is hydrogen or methyl, and * indicates the atom attached to the 6a-position of the tricyclic ring; and
$R_2$ is straight or branched chain $C_{1-6}$alkyl; tri-$C_{1-3}$alkylsilyl; a group of the formula

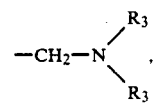

where each $R_3$, independently, is straight or branched chain $C_{1-4}$alkyl, or the two $R_3$'s together with the nitrogen atom to which they are attached form a group of the formula

where n is an integer 4, 5 or 6, or a group of the formula

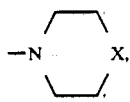

where X is —O—, —S— or —NCH₃; or a group of the formula

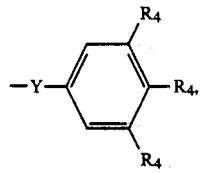

where Y is $(CH_2)_{1-3}$, —OCH₂— or —OCH₂CH₂—, and each R₄, independently, is hydrogen or C₁₋₃alkoxy; with the provisos that:
(1) only one of the R₁'s in (a), (b), (c) or (d) is methyl; and
(2) the R₂ substituent can only be in the 3'- or 4'-positions;
or a pharmaceutically acceptable acid addition salt thereof.

2. A compound according to claim 1 of formula I':

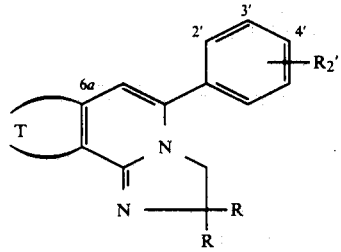

wherein

R₂' is straight or branched chain C₁₋₄alkyl; tri-C₁₋₃alkylsilyl; a group of the formula

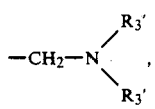

where the R₃''s are the same and are straight chain C₁₋₄alkyl, or the two R₃''s together with the nitrogen atom to which they are attached form a group of the formula

where n as is defined in claim 1, or a group of the formula

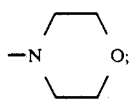

or a group of the formula

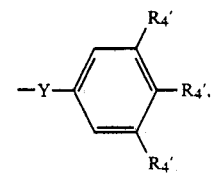

where Y is as defined in claim 1 and the R₄''s are the same and are C₁₋₃alkoxy;
and the R's and T are as defined in claim 1; with the provisos that:
(1) only one of the R₁'s in (a), (b), (c) or (d) is methyl; and
(2) the R₂' substituent can only be in the 3'- or 4'-positions;
or a pharmaceutically acceptable acid addition salt thereof.

3. A compound according to claim 2 of formula I':

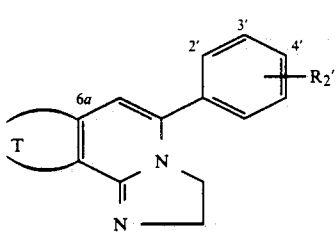

wherein T and R₂' are as defined in claim 2 and the foregoing provisos in claim 2 apply; or a pharmaceutically acceptable acid addition salt thereof.

4. A compound according to claim 3 having the formula

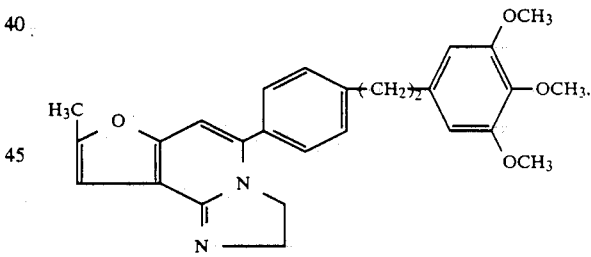

or a pharmaceutically acceptable acid addition salt thereof.

5. A compound according to claim 4 having the formula

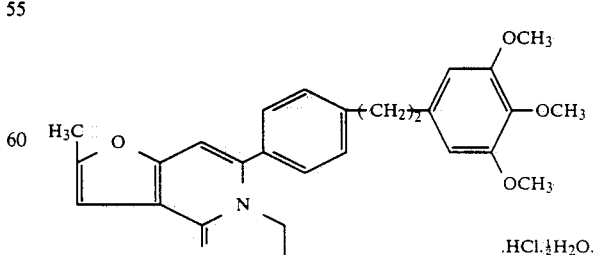

6. A compound according to claim 3 having the formula

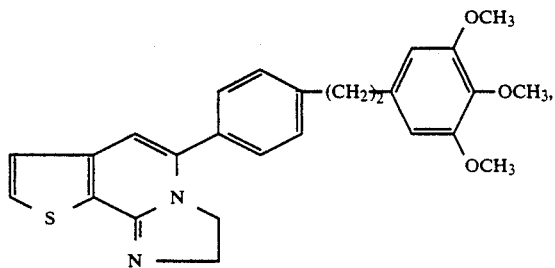

or a pharmaceutically acceptable acid addition salt thereof.

7. A compound according to claim 6 having the formula

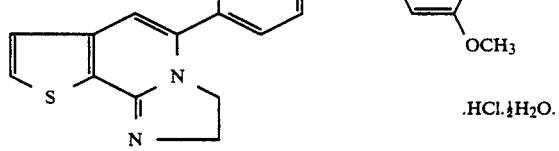

.HCl.½H₂O.

8. A compound according to claim 3 having the formula

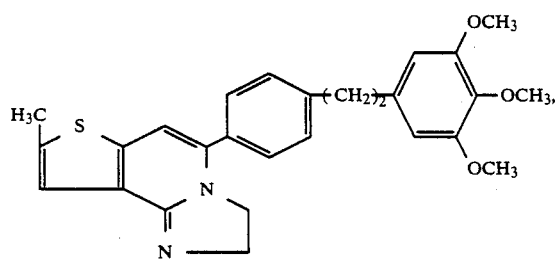

or a pharmaceutically acceptable acid addition salt thereof.

9. A compound according to claim 8 having the formula

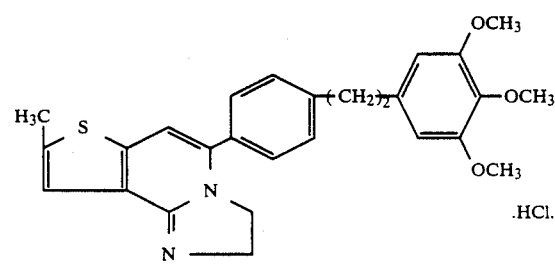

.HCl.

10. A compound according to claim 3 having the formula

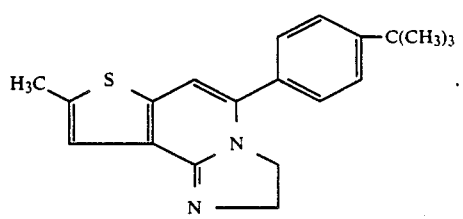

or a pharmaceutically acceptable acid addition salt thereof.

11. A compound according to claim 10 having the formula

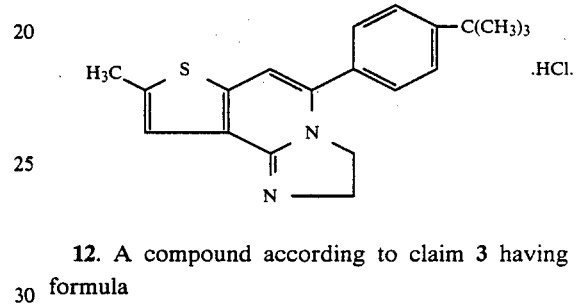

.HCl.

12. A compound according to claim 3 having the formula

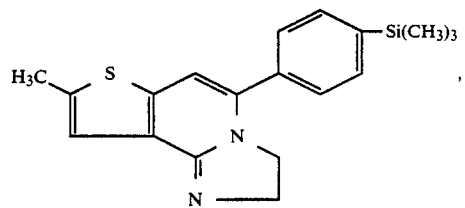

or a pharmaceutically acceptable acid addition salt thereof.

13. A compound according to claim 12 having the formula

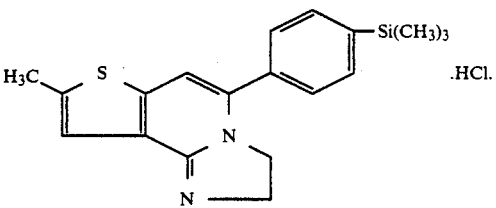

.HCl.

14. A method of inhibiting PAF-mediated bronchoconstriction and extravasation comprising administering to a subject afflicted therewith a therapeutically effective amount of a compound according to claim 1, or a pharmaceutically acceptable acid addition salt thereof.

15. A method according to claim 14 comprising administering a therapeutically effective amount of the compound of the formula

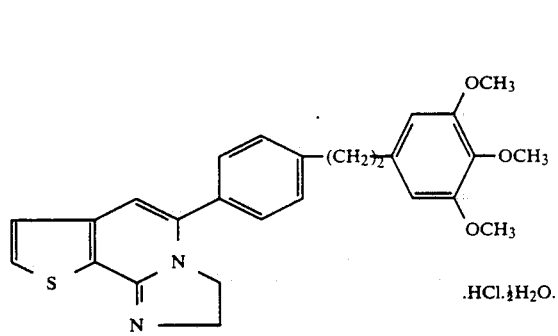

.HCl.½H₂O.

16. A method of controlling hyperreactive airways induced by PAF or allergen comprising administering to a subject afflicted therewith a therapeutically effective amount of a compound according to claim 1, or a pharmaceutically acceptable acid addition salt thereof.

17. A method according to claim 16 comprising administering a therapeutically effective amount of the compound of the formula

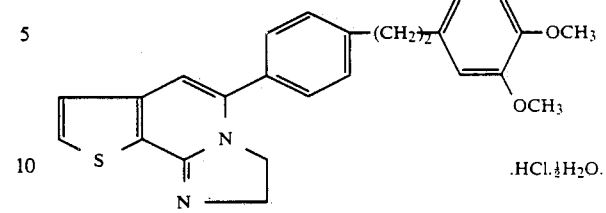

.HCl.½H₂O.

18. A method of protecting against endotoxin-induced hypotension comprising administering to a subject afflicted therewith a therapeutically effective amount of a compound according to claim 1, or a pharmaceutically acceptable acid addition salt thereof.

19. A method of protecting against endotoxin-induced death comprising administering to a subject afflicted therewith a therapeutically effective amount of a compound according to claim 1, or a pharmaceutically acceptable acid addition salt thereof.

20. A pharamaceutical composition useful in inhibiting PAF-mediated bronchoconstriction and extravasation, for controlling hyperreactive airways, for protecting against endotoxin-induced hypotension and death comprising a pharmaceutically acceptable carrier and a therapeutically effective amount of a compound according to claim 1, or a pharmaceutically acceptable acid addition salt thereof.

* * * * *